(12) United States Patent
Yao et al.

(10) Patent No.: US 8,994,409 B2
(45) Date of Patent: Mar. 31, 2015

(54) STIMULATOR AND METHOD FOR PROCESSING A STIMULATION SIGNAL

(71) Applicant: Agency for Science, Technology and Research, Singapore (SG)

(72) Inventors: Lei Yao, Singapore (SG); Minkyu Je, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 121 days.

(21) Appl. No.: 13/900,429

(22) Filed: May 22, 2013

(65) Prior Publication Data

US 2013/0314129 A1    Nov. 28, 2013

(30) Foreign Application Priority Data

May 22, 2012  (SG) .................................. 201203745

(51) Int. Cl.
*H03K 5/01* (2006.01)
*H03K 3/012* (2006.01)
*A61N 1/36* (2006.01)

(52) U.S. Cl.
CPC ............ *H03K 3/012* (2013.01); *A61N 1/36153* (2013.01)
USPC .................................... 327/100; 607/2; 607/4

(58) Field of Classification Search
USPC .......................................... 327/100; 607/2, 4
See application file for complete search history.

(56) References Cited

U.S. PATENT DOCUMENTS

| | | |
|---|---|---|
| 6,100,675 A | 8/2000 | Sudo |
| 7,406,351 B2 | 7/2008 | Wesselink |
| 8,886,332 B2 * | 11/2014 | Molnar et al. ................. 607/59 |
| 2002/0177882 A1 | 11/2002 | DiLorenzo |
| 2006/0253174 A1 | 11/2006 | King |
| 2008/0015657 A1 | 1/2008 | Haefner |
| 2009/0030477 A1 | 1/2009 | Jarrard |
| 2010/0114258 A1 * | 5/2010 | Donofrio et al. ............... 607/63 |
| 2011/0060387 A1 | 3/2011 | King et al. |
| 2011/0307032 A1 * | 12/2011 | Goetz et al. ...................... 607/59 |
| 2012/0095461 A1 | 4/2012 | Herscher et al. |
| 2012/0330384 A1 * | 12/2012 | Perryman et al. ............... 607/72 |
| 2013/0053910 A1 * | 2/2013 | Hareland ........................ 607/6 |

(Continued)

FOREIGN PATENT DOCUMENTS

| | | |
|---|---|---|
| GB | 2 388 927 A | 11/2003 |
| WO | WO 2005/046787 A1 | 5/2005 |
| WO | WO 2008/004204 A1 | 1/2008 |

OTHER PUBLICATIONS

Steven P. Hooker, et al., "Physiologic Effects of Electrical Stimulation Leg Cycle Exercise Training in Spinal Cord Injured Persons," Arch. Phys. Med. Rehabil., vol. 73, pp. 470-474, (May 1992).

(Continued)

*Primary Examiner* — Adam Houston
(74) *Attorney, Agent, or Firm* — Blakely, Sokoloff, Taylor & Zafman LLP

(57) ABSTRACT

Various embodiments provide a method for processing a stimulation signal. The method may include monitoring an output voltage on an electrode, the electrode being provided with the stimulation signal; determining whether the output voltage is lower than a threshold voltage; if it is determined that the output voltage is lower than the threshold voltage, modifying the waveform of the stimulation signal; and providing the modified stimulation signal to an object via the electrode.

20 Claims, 12 Drawing Sheets

(56) References Cited

U.S. PATENT DOCUMENTS

| | | | |
|---|---|---|---|
| 2013/0053911 A1* | 2/2013 | Hareland | 607/6 |
| 2013/0304174 A1* | 11/2013 | Langhals et al. | 607/118 |
| 2013/0314129 A1* | 11/2013 | Yao et al. | 327/100 |
| 2014/0228837 A1* | 8/2014 | Giovangrandi et al. | 606/34 |
| 2014/0249429 A1* | 9/2014 | Tran | 600/483 |
| 2014/0277288 A1* | 9/2014 | Archer | 607/62 |
| 2014/0278168 A1* | 9/2014 | Rogers | 702/63 |
| 2014/0324131 A1* | 10/2014 | Shi et al. | 607/72 |
| 2014/0330357 A1* | 11/2014 | Stevenson et al. | 607/116 |
| 2014/0336514 A1* | 11/2014 | Peyman | 600/473 |
| 2014/0336727 A1* | 11/2014 | Perryman et al. | 607/59 |

OTHER PUBLICATIONS

William W.L. Glenn, et al., "Twenty Years of Experience in Phrenic Nerve Stimulation to Pace the Diaphragm," Pacing and Clinical Electrophysiology, vol. 9, pp. 780-784, (Nov.-Dec. 1986).

Alexis M. Kuncel, et al., "Selection of Stimulus Parameters for Deep Brain Stimulation," Clinical Neurophysiology, vol. 115, pp. 2431-2441, (2004).

Tushar R. Gheewala, et al., "A CMOS Implantable Multielectrode Auditory Stimulator for the Deaf," IEEE Journal of Solid-State Circuits, vol. SC-10, No. 6, pp. 472-479, (Dec. 1975).

O. H. Schmitt, et al., "Scientific Apparatus and Laboratory Methods: A Universal Precision Stimulator," Science, vol. 76, No. 1971, p. 328, (Oct. 1932).

Jongwoo Lee, et al., "A 64 Channel Programmable Closed-Loop Neurostimulator with 8 Channel Neural Amplifier and Logarithmic ADC," IEEE Journal of Solid-State Circuits, vol. 45, No. 9, pp. 1935-1945, (Sep. 2010).

Kuanfu Chen, et al., "An Integrated 256-Channel Epiretinal Prosthesis," IEEE Journal of Solid-State Circuits, vol. 45, No. 9, pp. 1946-1956, (Sep. 2010).

Maurits Ortmanns, et al., "A 232-Channel Epiretinal Stimulator ASIC", IEEE Journal of Solid-State Circuits, vol. 42, No. 12, pp. 2946-2959, (Dec. 2007).

Shuenn-Yuh Lee, et al., "An Implantable Wireless Bidirectional Communication Microstimulator for Neuromuscular Stimulation," IEEE Transactions on Circuits and Systems—I: Regular Papers, vol. 52, No. 12, pp. 2526-2538, (Dec. 2005).

Meysam Azin, et al., "A Battery-Powered Activity-Dependent Intracortical Microstimulation IC for Brain-Machine-Brain Interface," IEEE Journal of Solid-State Circuits, vol. 46, No. 4, pp. 731-745, (Apr. 2011).

Maysam Ghovanloo, "Switched-Capacitor Based Implantable Low-Power Wireless Microstimulating Systems," IEEE International Symposium on Circuits and Systems (ISCAS) 2006, pp. 2197-2200, (May 2006).

Almut Branner, et al., "Long-Term Stimulation and Recording with a Penetrating Microelectrode Array in Cat Sciatic Nerve," IEEE Transactions on Biomedical Engineering, vol. 51, No. 1, pp. 146-157, (Jan. 2004).

Kriangkrai Sooksood, et al., "A Neural Stimulator Front-End with Arbitrary Pulse Shape, HV Compliance and Adaptive Supply Requiring $0.05mm^2$ in $0.35\mu m$ HVCMOS," IEEE international Solid-State Circuits Conference (ISSCC) 2011, Session 17, pp. 306-308, (Feb. 22, 2011).

Scott K. Arfin, et al., "An Energy-Efficient, Adiabatic Electrode Stimulator with Inductive Energy Recycling and Feedback Current Regulation," IEEE Transactions on Biomedical Circuits and Systems, vol. 6, No. 1, pp. 1-14, (Feb. 2012).

Shawn K. Kelly, et al., "A Power-Efficient Neural Tissue Stimulator With Energy Recovery," IEEE Transactions on Biomedical Circuits and Systems, vol. 5, No. 1, pp. 20-29, (Feb. 2011).

Emilia Noorsal, et al., "A Neural Stimulator Frontend with High-Voltage Compliance and Programmable Pulse Shape for Epiretinal Implants," IEEE Journal of Solid-State Circuits, vol. 47, No. 1, pp. 1-13, (Jan. 2012).

Daniel R. Merrill, et al., "Electrical Stimulation of Excitable Tissue: Design of Efficacious and Safe Protocols," Journal of Neuroscience Methods, vol. 141, pp. 171-198, (2005).

H. Bostock, "The Strength-Duration Relationship for Excitation of Myelinated Nerve: Computed Dependence on Membrane Parameters," Journal of Physiology, vol. 341, pp. 59-74, (1983).

Ilona Mogyoros, et al., "Strength-Duration Properties of Human Peripheral Nerve," Brain, vol. 119, pp. 439-447, (1996).

Singapore Written Opinion of the Danish Patent and Trademark Office for Counterpart Singapore Patent Application No. 201303976-3, 10 pgs., (Jul. 11, 2014).

Singapore Search Report of the Danish Patent and Trademark Office for Counterpart Singapore Patent Application No. 201303976-3, 9 pgs., (Jul. 11, 2014).

K. Sooksood et al., "A Neural Stimulator Front-End with Arbitrary Pulse Shape, HV Compliance and Adaptive Supply Requiring $0.05mm^2$ in $0.35\mu m$ HVCMOS," Solid-State Circuits IEEE International Conference—ISSCC, pp. 306-308 (2011).

* cited by examiner

STIMULATOR AND METHOD FOR PROCESSING A STIMULATION SIGNAL

CROSS-REFERENCE TO RELATED APPLICATIONS

The present application claims the benefit of the Singapore patent application 201201745-3 filed on 22 May 2012, the entire contents of which are incorporated herein by reference for all purposes.

TECHNICAL FIELD

Embodiments relate generally to a stimulator and a method for processing a stimulation

BACKGROUND

Neural and muscular electrical stimulation has been used as an effective method in clinical treatment for neurological and physiological disorders for decades since the first fully electrical based stimulator was reported in early 1930s. In recent years, advanced semiconductor technology is taken advantage of to implement the stimulators for implantable biomedical applications, such as deep brain stimulation (DBS), retinal/cochlear prosthesis, functional electrical stimulation (FES) and brain to brain interface. Power efficiency of these implantable stimulators becomes increasingly important, since the power needs to be minimized to avoid frequent battery changing or to adapt a smaller power transmission coil.

There are basically three stimulation modes for a stimulator: voltage mode, charge mode and current mode. Voltage mode has the highest power efficiency but is rarely used in modern stimulators. The main problem of the voltage mode is that it cannot provide control on the total stimulation charge/energy as the load impedance is varying over time, probe location and stimulation polarity. The uncontrollable charge/energy may lead to serious safety issue. Charge mode can accurately control the stimulation energy and achieve high power efficiency. However, it requires very large capacitors (~µF) to deliver sufficient charge/energy into the stimulation site. Thus the charge mode may not be suitable for implantable applications. Current mode is the most popular mode used in the stimulators because of its safety and effectiveness over a wide range of load impedance. Its major drawback is the low power efficiency which is of great importance for these advanced implantable stimulators.

The low power efficiency of current mode stimulators originates from the nature of the bioelectrical interface between the stimulator and the targeted neuron/muscle tissue. Variable or unpredictable site impedance is one of the main sources responsible for the energy efficiency drop. In a stimulation system, for example, a stimulation system 100 as shown in FIG. 1, the load impedance 104 for a stimulator 102 includes stimulation probe impedance and tissue impedance. The load impedance may vary when using different shaped probes 106 or at different stimulation sites 108 when stimulating different body tissue as shown in FIG. 1. Moreover, the load impedance may change over time in the chronic clinical stimulation. Thus, the maximum load impedance must be accommodated in the stimulator design, which means enough voltage compliance must be provided for a certain current level. For example, in the case of 1 mA current stimulation with 10 kΩ resistive load, ideally 10V voltage compliance needs to be provided by the stimulator. In most of the stimulators a fixed high voltage power supply is used to provide the high voltage compliance. In another case, for example when the 10 kΩ load is changing to a smaller value of 1 kΩ for some reason such as switching to other stimulation site or probe movement, assuming the stimulation current is still kept as 1 mA, the power efficiency drops dramatically from ideal 100% to 10%. This power efficiency problem is illustrated in FIG. 1, wherein when the load impedance is high ($R_{high}$), the $V_{over\text{-}head}$ is small and the wasted power $P_w$ is low. Accordingly, the power efficiency is about 80%. When the load impedance is low ($R_{low}$), the $V_{over\text{-}head}$ is large and the wasted power $P_w$ is high. In that case, the power efficiency is about 20%.

Closed loop configuration is widely used in many stimulation systems. Many research groups are now working to improve the power efficiency for the current mode stimulators based on closed loop supply voltage adaptation method.

In the supply voltage adaptation method (e.g. as shown in FIGS. 2A and 2B), the supply voltage of the output stage VDD_h is varying based on the load impedance. Two important building blocks are required for this method: 1) impedance detection block to acquire the load impedance information and 2) the adaptive supply block (DC-DC convener) to adjust the supply voltage so as to increase the power efficiency.

FIG. 2A shows a diagram of an adaptive power supply stimulator 200. The stimulator 200 includes a digital control block 202, a digital to analog converter 204 (DAC), a high voltage output stage 206 (HVOS), a high voltage (HV) monitoring block 208 and a DC-DC converter 210. The HV monitoring block 208 is used as the impedance detection block, since the voltage on the stimulation electrode is proportional to the load impedance. The voltage across the load is the direct indication of the power efficiency.

FIG. 2B shows a chart 250 illustrating the supply voltage adaptation provided by the adaptive power supply stimulator 200. Using a simplified resistive dummy load, the stimulation signal (e.g. the stimulation current) used in the supply voltage adaptation may have the same stimulation waveform as the voltage 260 on the stimulation electrode, e.g. a square stimulation waveform of the voltage 260. As shown in FIG. 2B, when the voltage 260 on the stimulation electrode is detected to be low, e.g., when low load impedance $R_{low}$ is detected wherein the power efficiency is indicated to be about 20% as in FIG. 1 above, the DC-DC converter 210 is used to adjust the supply voltage VDD_h 270 to a lower value. This would help to improve the power efficiency to be about 80%.

In K. Sooksood el al. "A Neural Stimulator Front-End with Arbitrary Pulse Shape, HV Compliance and Adaptive Supply Requiring 0.05 mm² in 0.35 µm HVCMOS," in IEEE ISSCC 2011, pp. 306-307, a high voltage comparator is used to detect the output voltage. This voltage comparator is used to control a two-level (20V and 5V) supply for the output stage. The estimated power efficiency for the output stage is from 20% to 90% using 100 µA stimulation current with 1ms duration on the load impedance ranging from 10 kΩ to 100 kΩ.

The supply voltage adaptation approach normally requires large inductors and consumes a lot of power. In some approaches, inductors and capacitors are required to provide different level of supply voltage to the output stage.

However, the supply voltage adaptation method requires extra circuit block (e.g. DC-DC converter) that causes extra power efficiency drop, and requires large inductors/capacitors for each voltage level and each channel, which may not be suitable for implantable applications. The resolution for voltage levels is also low.

SUMMARY

Various embodiments provide a method for processing a stimulation signal. The method may include monitoring an output voltage on an electrode, the electrode being provided with the stimulation signal; determining whether the output voltage is lower than a threshold voltage; if it is determined that the output voltage is lower than the threshold voltage, modifying the waveform of the stimulation signal; and providing the modified stimulation signal to an object via the electrode.

BRIEF DESCRIPTION OF THE DRAWINGS

In the drawings, like reference characters generally refer to the same parts throughout the different views. The drawings are not necessarily to scale, emphasis instead generally being placed upon illustrating the principles of the invention. In the following description, various embodiments are described with reference to the following drawings, in which.

DESCRIPTION

Various embodiments provide a stimulator and a method for processing a stimulation signal, which can achieve high power efficiency without requiring area consuming components.

Various features described below in the context of the method for processing a stimulation signal may analogously hold true for the stimulator, and vice versa.

In this context, the stimulator as described in this description may include a memory which is for example used in the processing carried out by the stimulator. A memory used in the embodiments may be a volatile memory, for example a DRAM (Dynamic Random Access Memory) or a non-volatile memory, for example a PROM (Programmable Read Only Memory), an EPROM (Erasable PROM), EEPROM (Electrically Erasable PROM), or a flash memory, e.g., a floating gate memory, a charge trapping memory, an MRAM (Magnetoresistive Random Access Memory) or a PCRAM (Phase Change Random Access Memory).

In this context, the stimulator as described in this description may be or may include one or more circuits for carrying out the method of processing a stimulation signal.

In an embodiment, a "circuit" may be understood as any kind of a logic implementing entity, which may be special purpose circuitry or a processor executing software stored in a memory, firmware, or any combination thereof. Thus, in an embodiment, a "circuit" may be a hard-wired logic circuit or a programmable logic circuit such as a programmable processor, e.g. a microprocessor (e.g. a Complex Instruction Set Computer (CISC) processor or a Reduced Instruction Set Computer (RISC) processor). A "circuit" may also be a processor executing software, e.g. any kind of computer program, e.g. a computer program using a virtual machine code such as e.g. Java. Any other kind of implementation of the respective functions which will be described in more detail below may also be understood as a "circuit" in accordance with an alternative embodiment.

Figure 3:
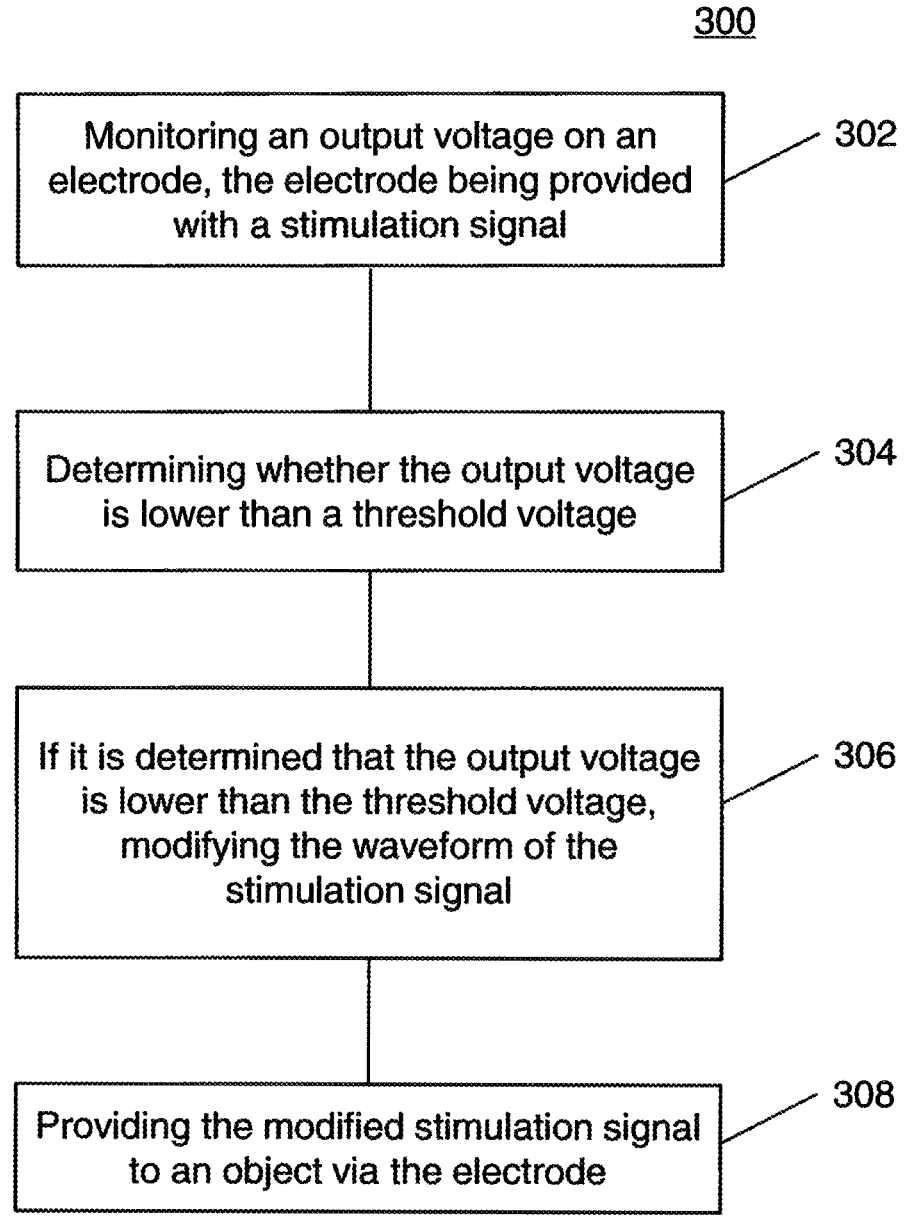
FIG. 3 shows a flowchart illustrating a method for processing a stimulation signal according to various embodiments.

FIG. 3 shows a flowchart 300 illustrating a method for processing a stimulation signal according to various embodiments.

At 302, an output voltage on an electrode may be monitored, wherein the electrode may be provided with a stimulation signal, e.g. generated by a stimulator.

At 304, it is determined whether the output voltage is lower than a threshold voltage.

At 306, if it is determined that the output voltage is lower than the threshold voltage, the waveform of the stimulation signal may be modified.

At 308, the modified stimulation signal may be provided to an object via the electrode.

In various embodiments, if it is determined that the output voltage is higher than or equal to the threshold voltage, the stimulation signal may be provided to the electrode, e.g. without being modified.

In various embodiments, the threshold voltage may be a predetermined voltage. In various embodiments, the threshold voltage may be determined based on a supply voltage (e.g. a supply voltage provided to a stimulator). By way of example, the threshold voltage may be determined to be about 20%-70% of the supply voltage, e.g., 20% of the supply voltage, 30% of the supply voltage, 40% of the supply voltage, 50% of the supply voltage, 60% of the supply voltage, etc., such that when the output voltage is below this threshold voltage, the corresponding power efficiency may not be satisfactory.

In various embodiments, the waveform of the stimulation signal may be modified such that the modified stimulation signal provides a constant charge as compared to an original stimulation signal. In this context, the original stimulation signal refers to the stimulation signal before waveform modification, in other words, the initial stimulation signal provided to the electrode.

In various embodiments, the waveform of the stimulation signal may be modified such that the modified stimulation signal provides higher power efficiency as compared to the original stimulation signal.

In various embodiments, modifying the waveform of the stimulation signal may include modifying at least one of the amplitude, the duration (e.g. pulse width), or the shape of the stimulation signal. In various embodiments, the stimulation signal may be a pulse signal including a pulse, or a pulse signal including two or more pulses with different polarities, or a pulse signal including two or more pulses with alternately different polarities. In various embodiments, the stimulation signal may be a pulse train of pulses having the same polarity or different polarities. The pulse signal including one or more pulses may be repeated or iterated at predetermined intervals, e.g. every few microseconds, every few milliseconds, etc.

In various embodiments, the stimulation signal may be a current pulse signal. In various embodiments, modifying the waveform of the stimulation signal may include increasing the current amplitude of the stimulation signal and decreasing the duration (e.g. pulse width) of the stimulation signal. In various embodiments, the current amplitude may be increased and the duration may be decreased to an extent such that the modified stimulation signal provides higher power efficiency as compared to the original stimulation signal.

In various embodiments, modifying the waveform of the stimulation signal may include modifying the shape of the stimulation signal, such as modifying from one shaped signal to another shaped signal selected from square, rectangle, triangle, sine or sawtooth shaped waveforms. In various embodiments, modifying the waveform of the stimulation signal may include modifying at least one of the shape, the amplitude, or the duration (e.g. pulse width duration) of the stimulation signal.

According to various embodiments, modifying the waveform of the stimulation signal may include modifying one or more stimulation parameters and generating the modified stimulation signal based on the one or more stimulation parameters. In various embodiments, the stimulation parameters may include amplitude, duration (e.g. pulse width duration) and shape.

In various embodiments, the output voltage on the electrode may be monitored periodically or instantaneously.

Figure 4:
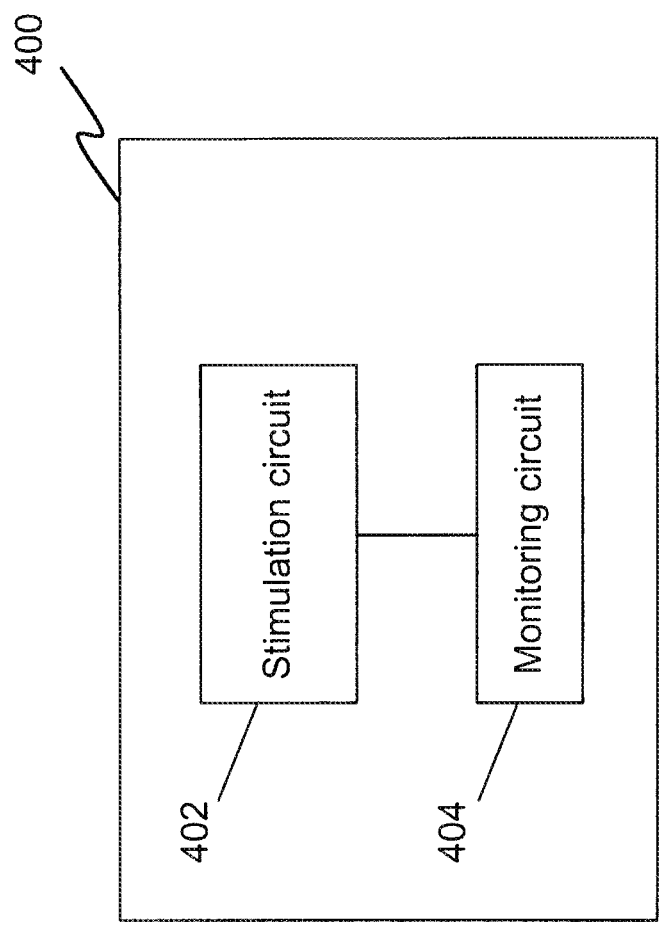
FIG. 4 shows a stimulator according to various embodiments.

FIG. 4 shows a stimulator according to various embodiments.

Various embodiments described in the context of the method of FIG. 3 above may analogously hold true for the stimulator of FIG. 4, and vice versa.

The stimulator 400 may include a stimulation circuit 402 configured to provide a stimulation signal to an object via an electrode; and a monitoring circuit 404 configured to monitor an output voltage on the electrode and determine whether the output voltage is lower than a threshold voltage.

The stimulation circuit 402 may be further configured to modify the waveform of the stimulation signal, and provide the modified stimulation signal to the electrode, if it is determined that the output voltage is lower than the threshold voltage.

In various embodiments, the stimulation circuit 402 may be configured to provide the stimulation signal to the electrode, if it is determined that the output voltage is higher than or equal to the threshold voltage.

In various embodiments, the threshold voltage may be a predetermined voltage, e.g. determined based on a supply voltage (e.g. a supply voltage provided to a stimulator) described above.

In various embodiments, the stimulation circuit 402 may be configured to modify the waveform of the stimulation signal such that the modified stimulation signal provides a constant charge as compared to an original stimulation signal. In various embodiments, the stimulation circuit 402 may be configured to modify the waveform of the stimulation signal such that the modified stimulation signal provides higher power efficiency as compared to the original stimulation signal. In this context, the original stimulation signal refers to the stimulation signal before waveform modification, in other words, the initial stimulation signal provided to the electrode.

According to various embodiments, the stimulation circuit 402 may be configured to modify at least one of the amplitude, the duration (e.g. pulse width), or the shape of the stimulation signal, if it is determined that the output voltage is lower than the threshold voltage. In various embodiments, the stimulation signal may be a pulse signal including a pulse, or a pulse signal including two or more pulses with different polarities, or a pulse signal including two or more pulses with alternately different polarities. In various embodiments, the stimulation signal may be a pulse train of pulses having the same polarity or different polarities. The pulse signal including one or more pulses may be repeated or iterated at predetermined intervals, e.g. every few microseconds, every few milliseconds, etc.

In various embodiments, the stimulation signal may be a current pulse signal. In various embodiments, the stimulation circuit 402 may be configured to increase the current amplitude of the stimulation signal and decrease the duration (e.g. pulse width) of the stimulation signal. In various embodiments, the current amplitude may be increased and the duration may be decreased to an extent such that the modified stimulation signal provides higher energy efficiency as compared to the original stimulation signal, if it is determined that the output voltage is lower than the threshold voltage.

According to various embodiments, the stimulation circuit 402 may include a controller (not shown) configured to modify one or more stimulation parameters, if it is determined by the monitoring circuit 404 that the output voltage is lower than the threshold voltage. The stimulation circuit 402 may further include a stimulation signal generator (not shown) configured to generate the stimulation signal based on the one or more stimulation parameters, and generate the modified stimulation signal based on the one or more modified stimulation parameters.

In various embodiments, the stimulation parameters may include amplitude, duration (e.g. pulse width duration) and shape.

In various embodiments, the controller included in the stimulation circuit 402 may be a digital controller comprising a state machine configured to modify the one or more stimulation parameters. The controller may also be an analog controller in other embodiments.

In various embodiments, the stimulation signal generator in the stimulation circuit 402 may include a digital to analog converter configured to convert the stimulation parameters into the stimulation signal, or convert the modified stimulation parameters into the modified stimulation signal.

According to various embodiments, the monitoring circuit 404 is configured to periodically or instantaneously monitoring the output voltage on the electrode.

According to various embodiments, the stimulator 400 may include a neurostimulator or a muscular stimulator.

The method for processing a stimulation signal and the stimulator of various embodiments will be described in more detail below.

Figure 5A:
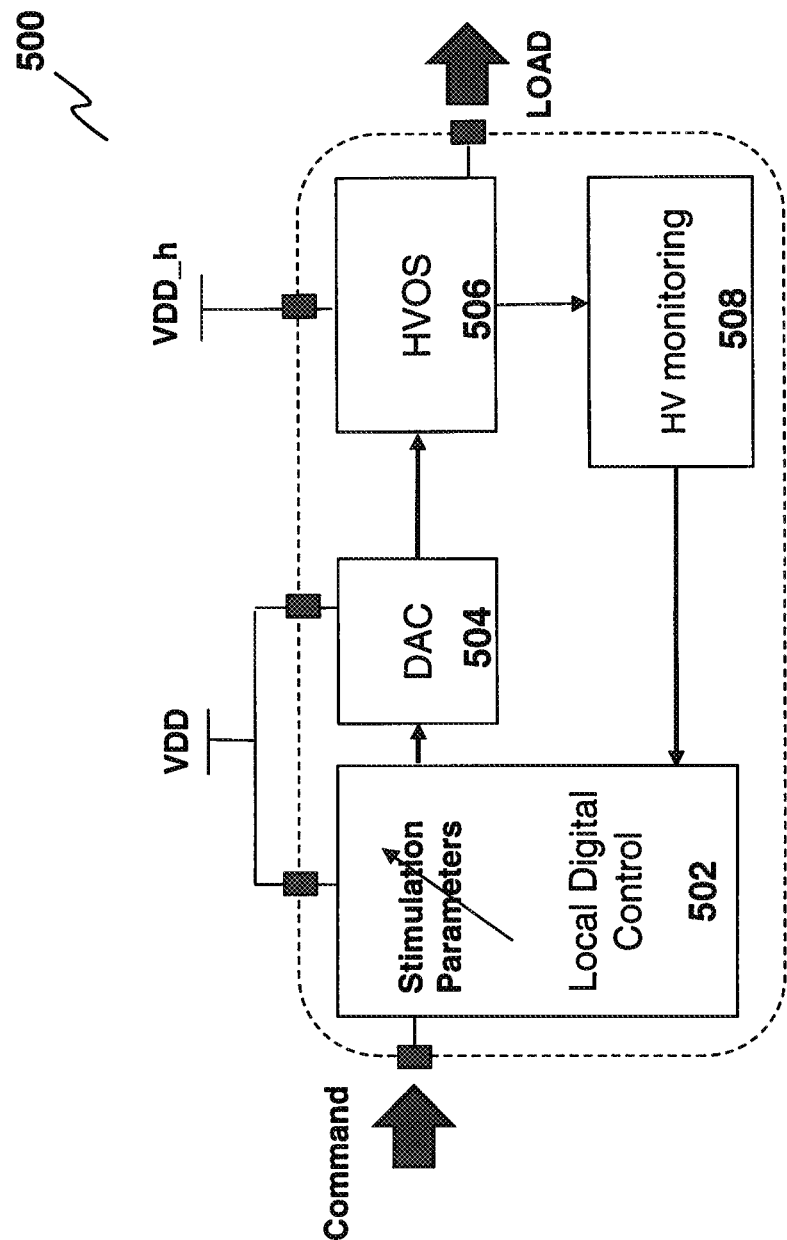
FIG. 5A shows a diagram of a stimulator according to various embodiments.
Figure 5B:
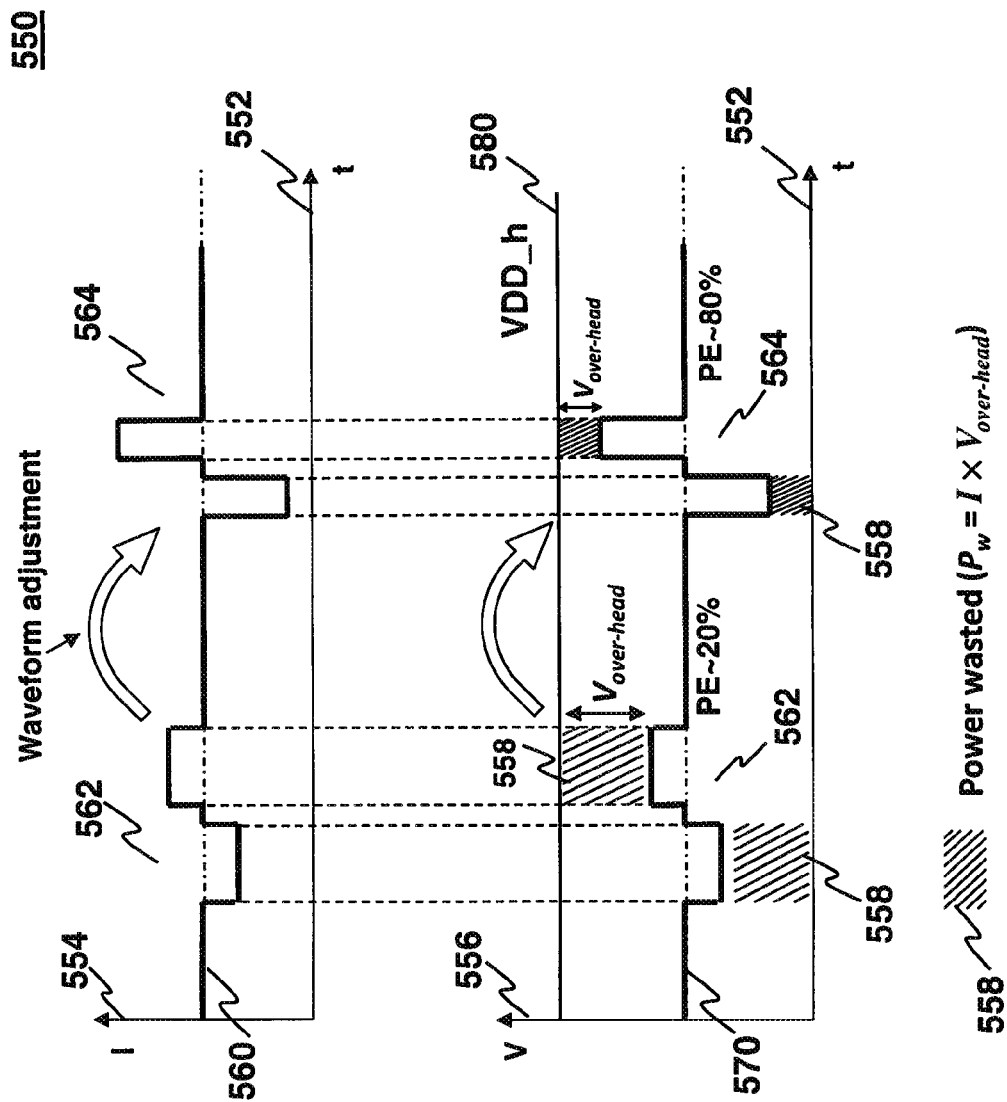
FIG. 5B shows a chart illustrating adjustment of stimulation signal by the stimulator according to various embodiments.

FIG. 5A shows a diagram of a stimulator 500 according to various embodiments; FIG. 5B shows a chart 550 illustrating adjustment of stimulation signal by the stimulator 500 according to various embodiments.

As shown in FIG. 5A, a stimulator 500 according to various embodiments may include a local digital controller (LDC) 502, a digital to analog converter (DAC) 504, a high voltage output stage (HVOS) 506 and a HV (high voltage) monitoring (HVM) block 508. Compared to the stimulator 200 of FIG. 2A, the DC-DC converter is eliminated from the stimulator 500.

The LDC 502 may receive serial commands from external blocks, such as a wireless receiver. The LDC 502 may decode the received command and store the stimulation parameters (e.g., amplitude, duration, waveform, etc.) in local registers. The LDC 502 may also control the stimulation timing of the HVOS 506, e.g. when to provide a stimulation signal to an object.

The DAC 504 may convert the digital data (e.g. the stimulation parameters) stored in the register into corresponding stimulation current level.

The HVOS 506 may amplify the DAC current which may be provided to a load, e.g. an electrode. The HVOS 506 may provide high voltage compliance using a high voltage supply (VDD_h).

The HVM 108 may monitor the output voltage of the HVOS 506 which is the voltage on the load. e.g. on the stimulation electrode. The HVM 508 may feed the monitored voltage information back to the LDC 502. The LDC 502 may modify or maintain the waveform of the stimulation signal provided to the load according to the method of various embodiments By way of example, the LDC 502, e.g. a state machine embedded in the LDC 502, may adjust the stimulation waveform parameters (e.g., amplitude, duration, shape, etc.) according to the method of various embodiments.

FIG. 5B shows adjustment of the stimulation signal by the stimulator 500 according to various embodiments.

In FIG. 5B, the current-time (I-t) Curie of the stimulation signal 560 and the voltage-time (V-t) curve of the output voltage 570 are shown, wherein the axis 552 represents the time (t), the axis 554 represents the current (I), and the axis 556 represents the voltage (V). In various embodiments illustrated in FIG. 5B, the stimulation signal 560 is a square wave signal, but it is understood that the stimulation signal 560 may be other types of wave signals. When the load impedance becomes low, the output voltage 570 at the load is low, e.g. as depicted at 562 and accordingly the wasted power depicted by 558 is high.

Figure 1:
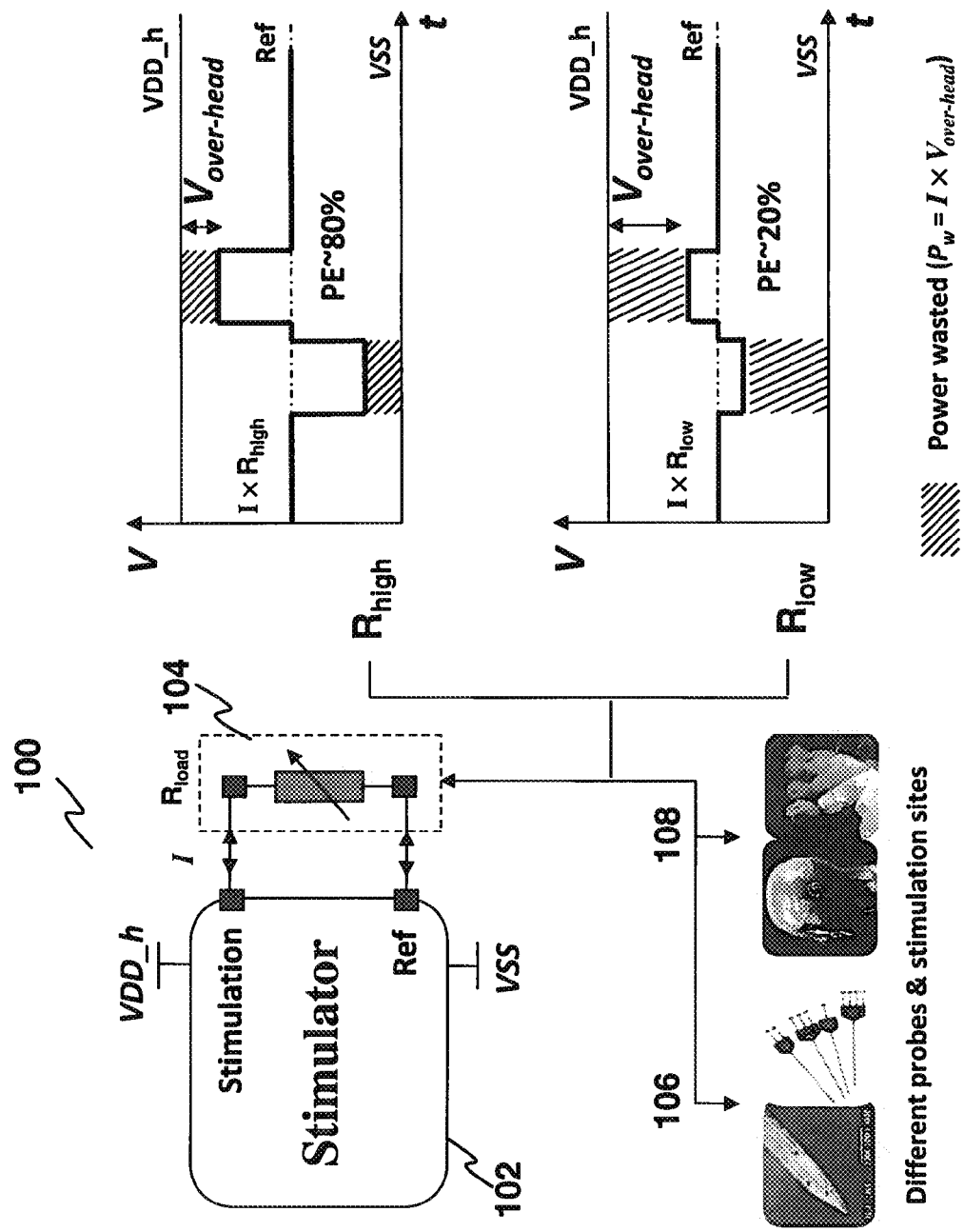
FIG. 1 shows a stimulation system.
Figure 2A:
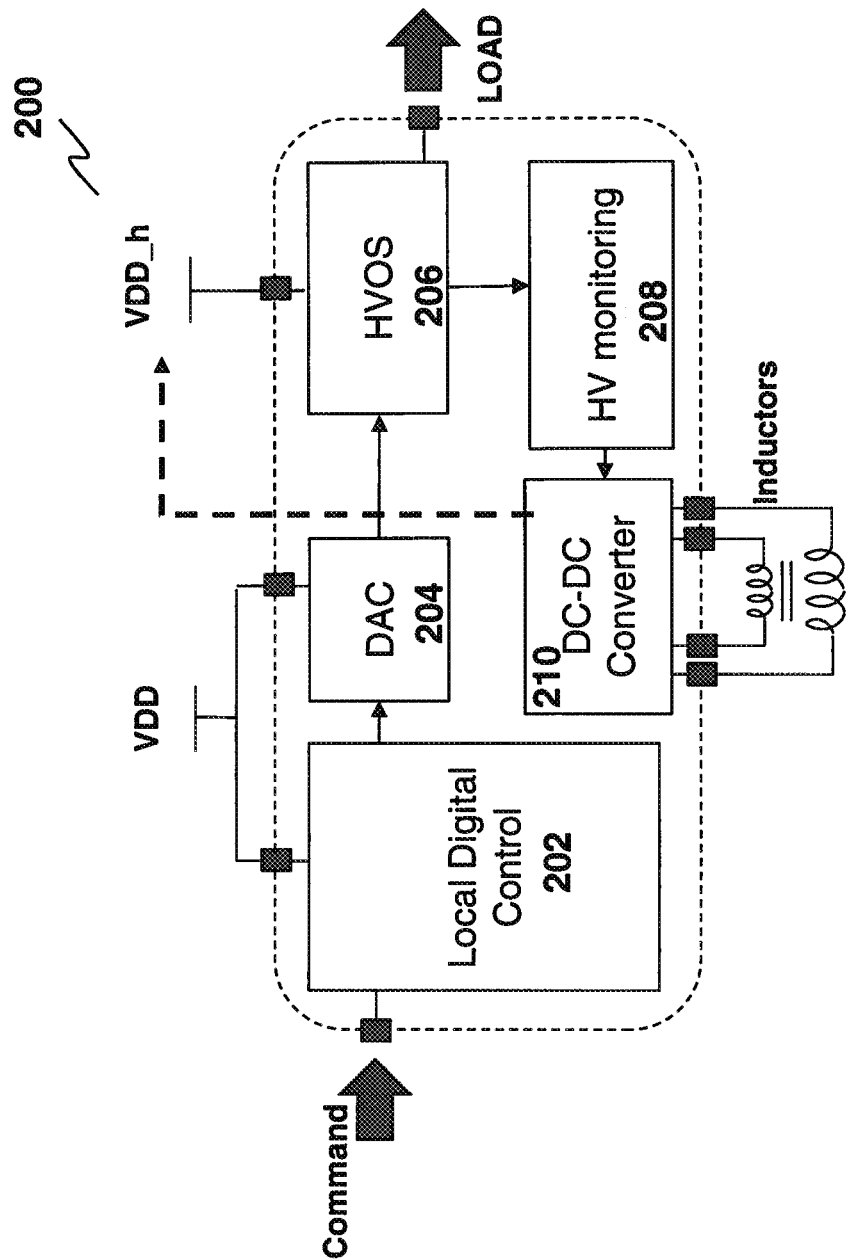
FIG. 2A shows a diagram of a supply voltage adaptation stimulator.
Figure 2B:
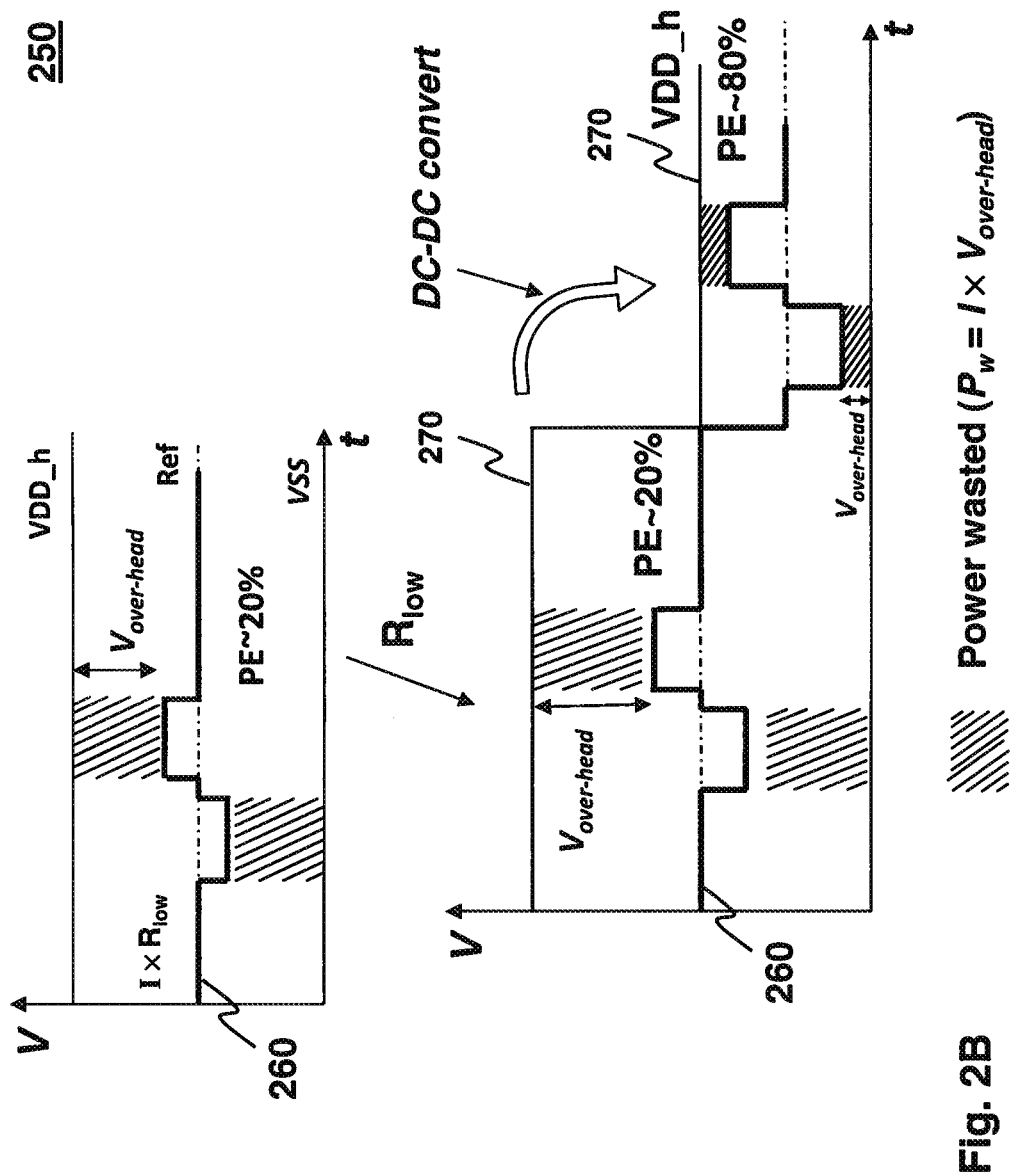
FIG. 2B shows the adaptive supply voltage provided by the supply voltage adaptation stimulator.

In various embodiments when the monitored output voltage 570 is determined to be lower than a threshold voltage, e.g. when the corresponding power efficiency (PE) is lowered to about 20% as depicted at 562, the LDC 502 may be configured to modify the waveform of the stimulation signal 560 to trace the supply voltage VDD_h 580, instead of adjusting the supply voltage VDD_h 580 to accommodate the waveform of the stimulation signal 560 as in FIG. 2B. In various embodiments as shown in FIG. 5B, the LDC 502 may be configured to modify the waveform of the stimulation signal 560 by increasing the current amplitude of the stimulation signal and decreasing the duration (e.g. pulse width) of the stimulation signal as depicted at 564. In various embodiments, the modified stimulation signal 560 having a waveform depicted at 564 may provide higher power efficiency as compared to the stimulation signal 560 having a waveform depicted at 562 before modification, as shown in the corresponding voltage-time curve wherein the output voltage 570 at the corresponding location 564 is increased to improve the power efficiency to be about 80%. The stimulation signal 560 having a modified waveform at 564 keeps the wasted voltage low and accordingly the wasted power 558 at 564 is low.

FIG. 5B shows that the waveform of the stimulation signal at 562 is modified to the waveform at 564 after an entire period of the stimulation signal 560, which is for illustration purpose only. It is understood that the waveform of the stimulation signal 560 may be modified during the initial period of the stimulation signal 560 or after several periods of the stimulation signal 560, when the corresponding output voltage is low enough. By way of example, when the HVM 508 is configured to instantaneously monitor the output voltage, the output voltage may be immediately detected to be lower than the threshold voltage, and the stimulation signal 560 may be modified immediately, e.g. during the initial period. By way of example, when the HVM 508 is configured to periodically monitor the output voltage, the output voltage may be determined to be lower than the threshold voltage after one or more periods of the simulation signal 560, and the stimulation signal 560 may be then modified.

The extent of modification to the waveform of the stimulation signal 560 (e.g. one or more of the amplitude, the duration, or the shape of the stimulation signal) may be determined such that a constant charge can be provided by the adjusted stimulation signal as compared to the initial stimulation signal. The extent of modification to one or more of the amplitude, the duration, or the shape of the stimulation signal 560 may also be determined based on constant bio-response to be achieved by the adjusted stimulation signal as compared to the initial stimulation signal, e.g. by using the charge-duration relationship between stimulation amplitude and stimulation duration.

The energy efficiency may be defined according to equation (1)

$$E_{effi} = \frac{S}{E_{in}} = \frac{S}{V_{DD\_h} I_{stim} t_{stim}} \qquad (1)$$

in which S is the bio-response strength induced by the input energy $E_{in}$. In current-mode stimulator, S is independent to $V_{DD\_h}$ but is a function of $I_{stim}$ (stimulation current, e.g. the current amplitude of the stimulation signal) and $t_{stim}$ (duration or pulse width of the stimulation signal). In the waveform adaptation method of various embodiments, the stimulation waveform parameters $I_{stim}$ and $t_{stim}$ may be adjusted, instead of adjusting the supply voltage $V_{DD\_h}$, to obtain high energy efficiency. Since the bio-response strength S will change when $I_{stim}$ and $t_{stim}$ are modified, the relationship between $E_{effi}$ and the waveform parameters under fixed S may be derived. In order to achieve a fixed amount of bio-response strength ($S_0$), the relationship between $I_{stim}$ and $t_{stim}$ may be described by the known strength-duration characteristics as in equation (2) below:

$$t_{stim} = \frac{\tau_{SD}}{I_{stim} - I_{rh}} \bigg|_{S_0} \qquad (2)$$

in which $\tau_{SD}$ is the strength-duration time constant of a given stimulation configuration. $I_{rh}$ is Rheobase current which is the minimum required stimulation current. Compared to embodiments wherein the modified stimulation signal is to provide a constant charge as compared to the initial stimulation signal, the $t_{stim}$ can be smaller in the embodiments wherein the modified stimulation signal is to achieve constant bio-response, which means the input energy can be smaller ($E_{effi}$ can be higher) to achieve the same bio-response.

According to the embodiments of FIG. 5A and FIG. 5B, the percentage of wasted power is reduced, and thus the power efficiency is improved, e.g. to about 80%, when the load impedance is low.

Figure 6:
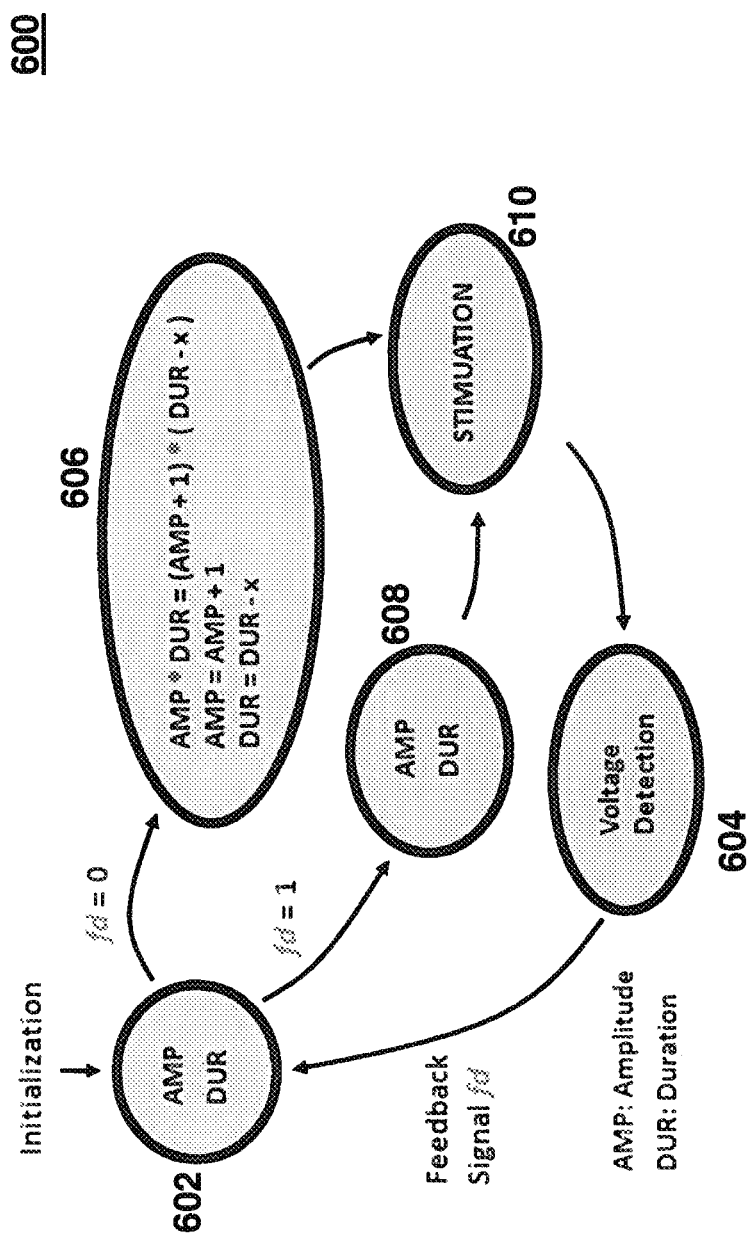
FIG. 6 illustrates the operation of a finite state machine according to various embodiments.

In various embodiments, the LDC 502 may include an embedded state machine configured to adjust the stimulation waveform parameters (e.g., amplitude, duration, shape, etc.) according to the method of various embodiments. FIG. 6 shows a diagram 600 illustrating the operation of the stage machine according to various embodiments.

At initialization, amplitude and duration of a stimulation signal may be provided at 602. Depending on a feedback signal fd provided by a voltage detection block 604, e.g. the HVM 508 of FIG. 5A, the state machine may adjust the stimulation waveform parameters accordingly.

When the feedback signal fd indicates that the load impedance is low, e.g. when the detected voltage at the load is lower than a predetermined threshold voltage which provides a feedback signal of fd=0, the amplitude parameter may be increased and the duration parameter may decreased at 606. The extent of adjustment to the amplitude parameter and the duration parameter may be determined such that a constant charge can be provided by the adjusted stimulation signal as compared to the initial stimulation signal. The extent of adjustment to the amplitude parameter and the duration parameter may also be determined based on a constant bioresponse to be achieved.

When the feedback signal fd indicates that the load impedance is high, e.g. when the detected voltage at the load is higher than or equal to the predetermined threshold voltage which provides a feedback signal of fd=1, the amplitude and duration parameters may be maintained at 608.

A stimulation signal generated according to the stimulation waveform parameters determined at 606 or 608 may be provided to the load for stimulation at 610.

The embodiments of FIG. 6 illustrate the adjustment of the amplitude and the duration parameters, it is understood that the shape parameters may also be adjusted. For example, the adjustment may be made by changing from one shaped wave signal to another shaped wave signal, and the examples of various shaped wave signal may include but are not limited to square, rectangle, triangle, sine or sawtooth wave signals.

Figure 7:
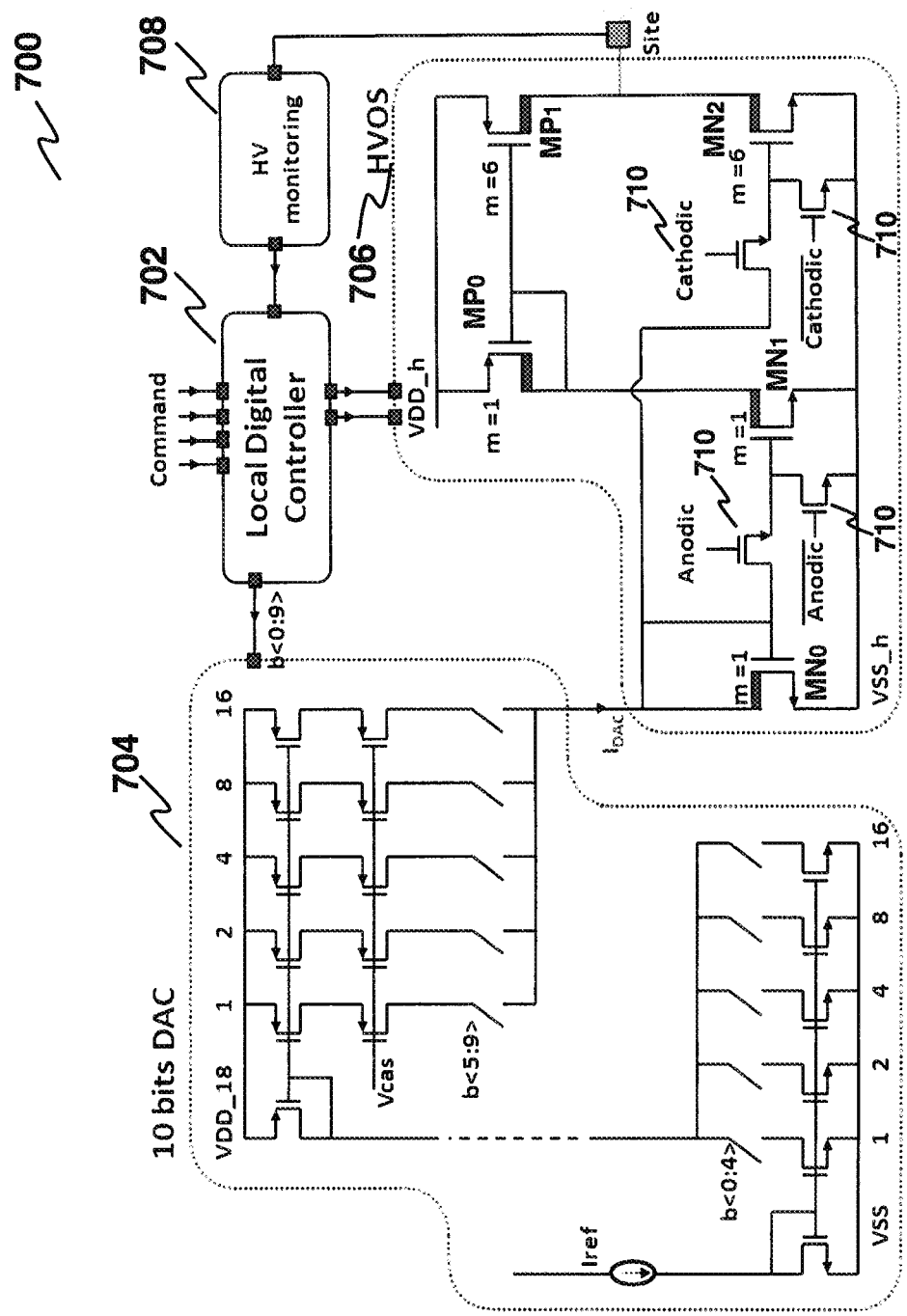
FIG. 7 shows a stimulator according to various embodiments.

FIG. 7 shows a stimulator 700 according to various embodiments.

FIG. 7 shows a schematic of the circuit diagrams and the interconnections among various circuit blocks of the stimulator 700 according to various embodiments, including the blocks of a local digital controller (LDC) 702, a 10-bits DAC 704, a HVOS 706 and a HV monitoring 708. These circuit blocks may be configured to carry out the processing similar to the blocks 502, 504, 506, 508 of FIG. 5A.

The stimulator 700 may provide power efficiency (at the output stage only) above 80%, using current stimulation signals equivalent to 100 μA current and 500 μs duration over the load impedance ranging from 10 kΩ to 100 kΩ.

In the embodiments of FIG. 7, the 10-bits DAC has a current steering DAC structure with non-cascode/cascode current sources controlled by an output b<0:9> from the LDC 702. The DAC input current $I_{ref}$ is set externally. The DAC output current $I_{DAC}$ is further amplified by the HVOS 706 which may include five high-voltage transistors ($MN_0$, $MN_1$, $MN_2$, $MP_0$ and $MP_1$) and four low voltage switching transistors 710. $I_{DAC}$ may be amplified 6 times and delivered to the load through $MN_0$ and $MN_2$ in cathodic phase, while in anodic phase $I_{DAC}$ may also be amplified 6 times and delivered to the load through $MN_0$, $MN_1$, $MP_0$ and $MP_1$.

Figure 8:
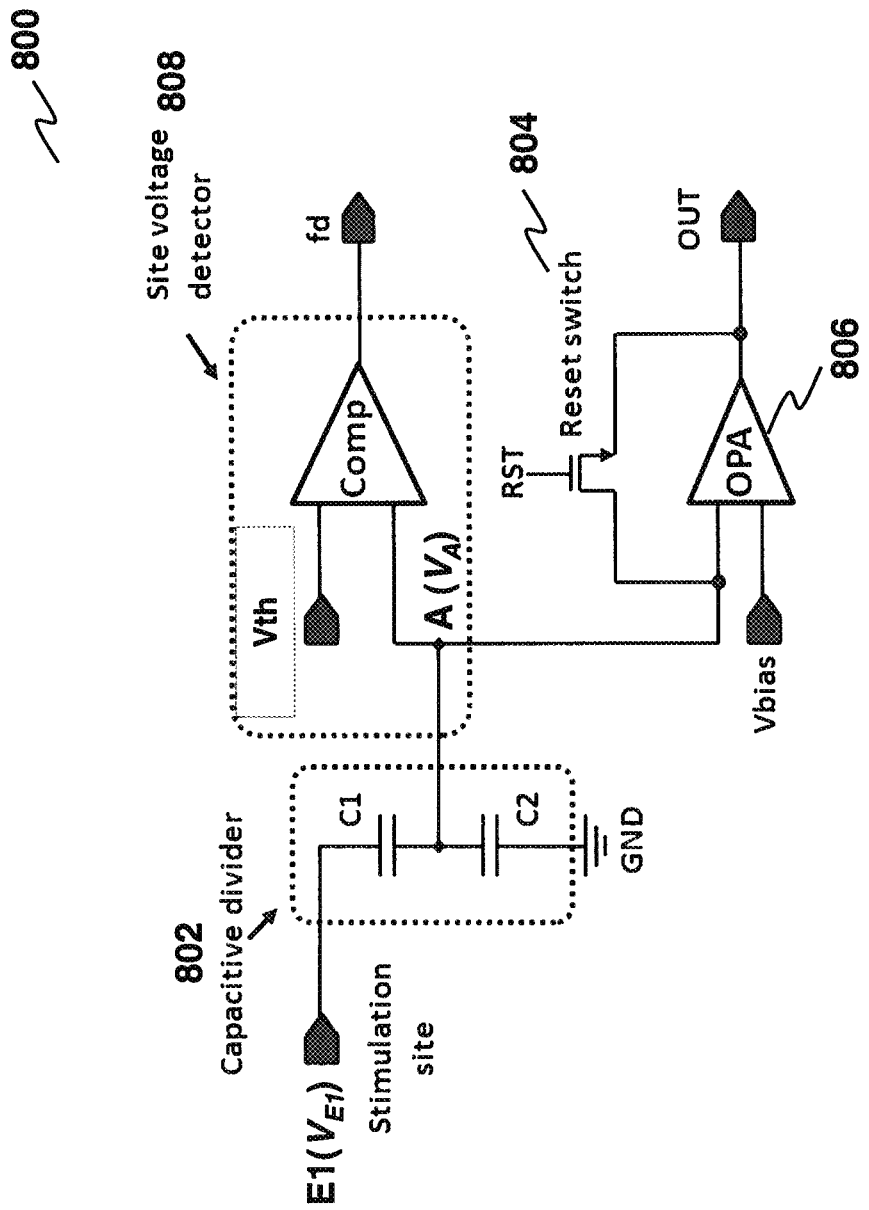
FIG. 8 shows a schematic of the HV monitoring block according to various embodiments.

FIG. 8 shows a schematic of the HV monitoring block 800 according to various embodiments. The HV monitoring block 800 may be used as the HVM 508 in FIG. 5A, or the HVM 708 in FIG. 7.

The HV monitoring block 800 may include a voltage divider 802 having two capacitors C1 and C2, which proportionally scales a high voltage (e.g., 0~20V) on the stimulation site to a low voltage (e.g. 0~3.3V) on an internal node A. Before each stimulation pulse, the two capacitors C1 and C2 may be respectively reset to a higher voltage reference Vcm (e.g. 10V) and a lower voltage reference Vcm_1 (e.g. 1.65V), through a reset switch 804 and an operational amplifier (OPA) 806. Voltage at node A, $V_A$, may be initialized to the lower voltage reference Vcm_1 of 1.65V by the voltage follower, i.e., the connected OPA 806.

During stimulation pulse the reset switch 804 is open and $V_A$ tracks the voltage ($V_{E1}$) on the stimulation site $E_1$. $C_1$ and $C_2$ may be chosen to be very small (~pF) so that the leakage current to $C_1$ and $C_2$ can be neglected during the stimulation. Meanwhile the value of $C_1$ and $C_2$ may also be chosen to be large enough to maintain a stable voltage in the presence of leakage current for the on-chip capacitor. In various embodiments, the ratio of $C_1$ to $C_2$ may be set to 1 pF:5 pF to make $V_A$ stay within the range from 0 to 4V while $V_{E1}$ ranges from 0 to 20V. The voltage at the stimulation site $V_{E1}$ may be monitored indirectly through monitoring $V_A$ which is in low voltage domain.

During the stimulation phase, the comparator of a site voltage detector 808 compares the voltage $V_A$ on node A to a threshold voltage Vth (e.g. the threshold voltage described in the embodiments above for comparison with the monitored output voltage on the electrode). If $V_A$ exceeds Vth, a logical high will be given (e.g. by provide a feedback signal fd=1) to indicate that the voltage on the electrode is large enough to maintain high power efficiency. If $V_A$ is smaller than Vth, a logical low will be given (e.g. by provide a feedback signal fd=0) to indicate that the voltage on the electrode is not large enough, and the LDC controller 502 or 702 shown in FIG. 5A and FIG. 7 will change the stimulation waveform parameters to achieve higher power efficiency, e.g. according to the algorithm shown in FIG. 6. The LDC controller 502 or 702 may, for example, increase the stimulation current amplitude and reduce the stimulation duration while keeping the same amount of stimulation charge/energy as illustrated in FIG. 5B.

The stimulator and the corresponding method described in various embodiments provide a closed loop control of system input parameters, e.g., stimulation parameters, with high voltage monitoring circuit. By adjusting the waveform of the stimulation signal to accommodate the power supply level, power efficiency is improved for varying or unpredictable load impedance.

The existing supply voltage adaptation method used in FIGS. 2A and 2B may heavily rely on the dynamic power supply, such as DC-DC converters. These dynamic power supplies themselves have low power efficiency problem, for example, the normal DC-DC conversion efficiency is about 75%, wherein 25% power efficiency is lost on the dynamic power supply block. Compared to the supply voltage adaptation method, the waveform adaptation method and stimulator of various embodiments can achieve higher power efficiency since there is no power efficiency drop on extra DC-DC converter circuit blocks.

Further, the supply voltage adaptation stimulator of FIG. 2A uses the dynamic power supply block (such as the DC-DC converter), which normally requires large inductors and capacitors which are difficult to be integrated on chip. The situation becomes worse when large number of stimulation channels is required. Each channel would require one dynamic power supply to provide a voltage according to the channel load impedance. For example, 100 stimulation channels would require 100 individual dynamic power supply blocks (e.g. requiring extra chip area of about 300 μm×300 μm/channel or off-chip components), which require 100 inductor/capacitors. Compared to the supply voltage adaptation stimulator of FIG. 2A, the waveform adaptation stimulator and method of various embodiments eliminate the dynamic power supply block and do not require area-consuming components such as large inductor or capacitor, which can provide faster stimulation suitable for very large number of stimulation channels and can also achieve reduced area and higher flexibility at reduced system complexity.

Figure 9:
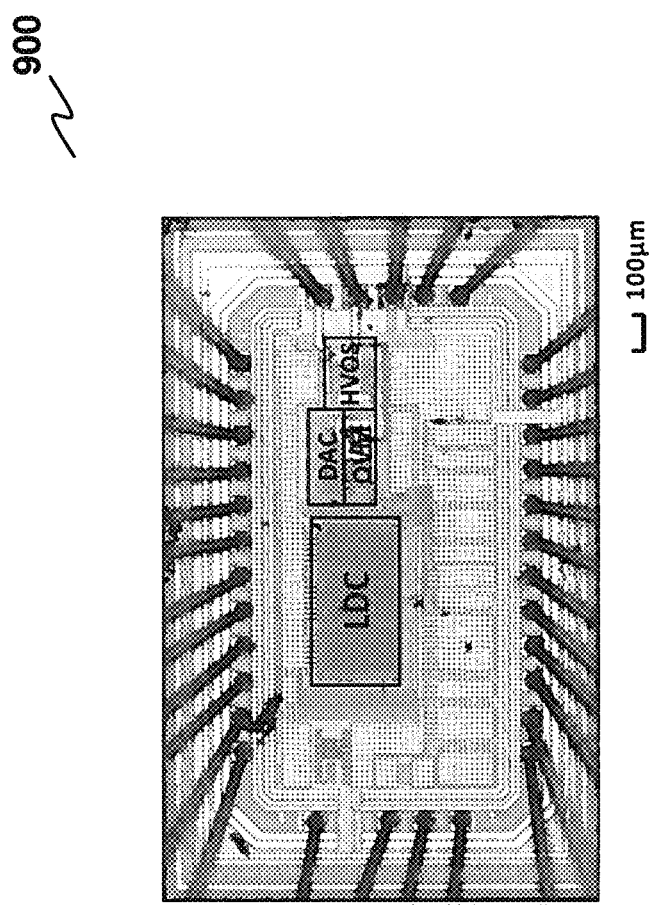
FIG. 9 shows the microphotography of a high voltage neural/muscular stimulator according to various embodiments.

The waveform adaptation method described in various embodiments above may be implemented in Global Foundry 0.18-μm CMOS HV process. The microphotography of a high voltage neural/muscular stimulator 900 (e.g. the stimulator 500, 700) fabricated in Global Foundry 0.18-μm CMOS 24V HV process is shown in FIG. 9. The stimulator 900 has high compliance voltage up to 24V accommodating high load impedance.

The stimulator 900 may use high voltage monitoring circuit (OVM) to detect output voltage on the stimulation electrode and use this information as feedback to adapt stimulation waveform. The waveform of the stimulation signal may be optimized based on the monitored voltage, for improved power efficiency over the varying load impedance. The stimulator 900 achieves a minimum power efficiency of 80% under 100 μA amplitude and 500 μs pulse width biphasical current stimulation with load impedance varying between 10 kΩ and 100 kΩ.

Figure 10:
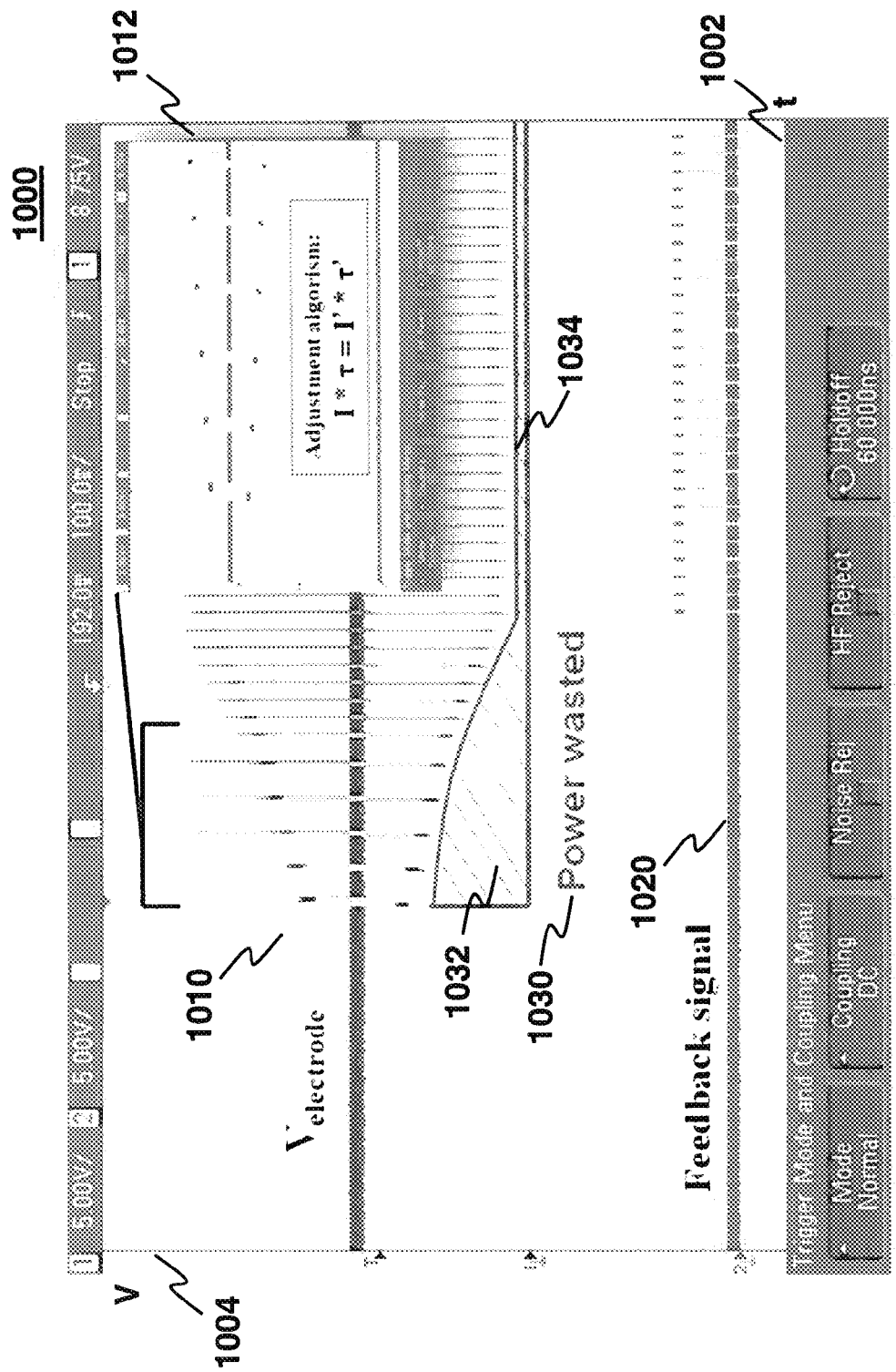
FIG. 10 shows a chart illustrating the measurement result using the method/stimulator of various embodiments.

FIG. 10 shows a chart 1000 illustrating the measurement result using the method/stimulator of various embodiments.

In FIG. 10, the measured stimulation waveform of the stimulator and the operation of the waveform adaptation method of various embodiments are shown. In FIG. 10, the voltage-time curve of the output voltage signal 1010 is shown, wherein the axis 1002 represents the time, and the axis 1004 represents the voltage. When the output voltage at the load is detected to be low enough, e.g. as indicated by the feedback signal 1020 (e.g. a low level of the feedback signal 1020), the wasted power depicted by 1030 is high at 1032.

In the waveform adaptation method according to various embodiments, when the wasted power is high enough, the waveform of the stimulation signal is adjusted to increase the current amplitude and to decrease the duration, and the waveform of the output voltage 1010 changes accordingly to have increased amplitude and decreased duration as shown in the enlarged view depicted at 1012. The waveform of the stimulation signal may be the same as the waveform of the output voltage 1010. In the embodiments shown in FIG. 10, a fixed charge algorithm is used which means the total charge delivered to the load is kept the same. The total charge may be represented by $Q=I*\tau=I'*\tau'$, wherein Q represents the charge, I and I' represent the initial current amplitude and the modified current amplitude, τ and τ' represent the initial duration and the modified duration. After the waveform adaptation, the wasted power 1030 is significantly reduced at 1034, and the stimulation signal does not need to be modified so that the corresponding output voltage 1010 maintains the same.

It should be noted that the algorism of the waveform adaptation method in various embodiments above can also be changed based on different applications. In the demonstration of FIG. 10, the initial pulse has a low power efficiency of 38%, and after the waveform adaptation the power efficiency is increased to 88%. For different load impedance the initial power efficiency may be different because the voltage drop on the load may be different. After the waveform adaptation optimization according to various embodiments, the power efficiency can be increased. The minimum power efficiency of 80% can be achieved over the impedance range from 10 kΩ to 100 kΩ when using 100 μA current and 500 μs duration as the initial condition in the stimulation.

The stimulator and the corresponding method described in various embodiments may be used for neural/muscle stimulation system, deep brain stimulation (DBS), spinal cord stimulation (SCS), functional electrical stimulation (FES), multi-channel recording, or other suitable stimulation systems. The stimulator and the corresponding method described in various embodiments may be used in many different applications such as implantable stimulation systems which require high power efficiency or large number of stimulation channels, or high frame speed stimulation systems.

While the invention has been particularly shown and described with reference to specific embodiments, it should be understood by those skilled in the art that various changes in form and detail may be made therein without departing from the spirit and scope of the invention as defined by the appended claims. The scope of the invention is thus indicated by the appended claims and all changes which come within the meaning and range of equivalency of the claims are therefore intended to be embraced.

What is claimed is:

1. A method for processing a stimulation signal, the method comprising:
    monitoring an output voltage on an electrode, the electrode being provided with the stimulation signal;
    determining whether the output voltage is lower than a threshold voltage;
    if it is determined that the output voltage is lower than the threshold voltage, modifying the waveform of the stimulation signal; and
    providing the modified stimulation signal to an object via the electrode.

2. The method of claim 1, further comprising:
    if it is determined that the output voltage is higher than or equal to the threshold voltage, providing the stimulation signal to the electrode.

3. The method of claim 1, further comprising
    modifying the waveform of the stimulation signal such that the modified stimulation signal provides higher power efficiency compared to an original stimulation signal.

4. The method of claim 1, further comprising
    modifying the waveform of the stimulation signal such that the modified stimulation signal provides a constant charge compared to an original stimulation signal.

5. The method of claim 1, wherein
    modifying the waveform of the stimulation signal comprises modifying at least one of the amplitude, the duration, or the shape of the stimulation signal.

6. The method of claim 1, wherein
    the stimulation signal is a current pulse signal.

7. The method of claim 6, wherein
    modifying the waveform of the stimulation signal comprises increasing the current amplitude of the stimulation signal and decreasing the duration of the stimulation signal.

8. The method of claim 1, wherein
    modifying the waveform of the stimulation signal comprises modifying one or more stimulation parameters and generating the modified stimulation signal based on the one or more stimulation parameters.

9. The method of claim 8, wherein
    the stimulation parameters comprise amplitude, duration and shape.

10. The method of claim 1, wherein
    monitoring the output voltage on the electrode comprises periodically or instantaneously monitoring the output voltage on the electrode.

11. A stimulator, comprising:
    a stimulation circuit configured to provide a stimulation signal to an object via an electrode;
    a monitoring circuit configured to monitor an output voltage on the electrode and determine whether the output voltage is lower than a threshold voltage;
    wherein the stimulation circuit is further configured to modify the waveform of the stimulation signal and provide the modified stimulation signal to the electrode, if it is determined that the output voltage is lower than the threshold voltage.

12. The stimulator of claim 11, wherein
the stimulation circuit is configured to provide the stimulation signal to the electrode, if it is determined that the output voltage is higher than or equal to the threshold voltage.

13. The stimulator of claim 11, wherein
the stimulation circuit is configured to modify the waveform of the stimulation signal such that the modified stimulation signal provides higher power efficiency compared to an original stimulation signal.

14. The stimulator of claim 11, wherein
the stimulation circuit is configured to modify the waveform of the stimulation signal such that the modified stimulation signal provides a constant charge compared to an original stimulation signal.

15. The stimulator of claim 11, wherein
the stimulation circuit is configured to modify at least one of the amplitude, the duration, or the shape of the stimulation signal, if it is determined that the output voltage is lower than the threshold voltage.

16. The stimulator of claim 11, wherein
the stimulation signal is a current pulse signal, and
the stimulation circuit is configured to increase the current amplitude of the stimulation signal and decrease the duration of the stimulation signal, if it is determined that the output voltage is lower than the threshold voltage.

17. The stimulator of claim 11, wherein the stimulation circuit comprises
a controller configured to modify one or more stimulation parameters, if it is determined by the monitoring circuit that the output voltage is lower than the threshold voltage; and
a stimulation signal generator configured to generate the stimulation signal based on the one or more stimulation parameters, and generate the modified stimulation signal based on the one or more modified stimulation parameters.

18. The stimulator of claim 17, wherein
the controller is a digital controller comprising a state machine configured to modify the one or more stimulation parameters.

19. The stimulator of claim 17, wherein
the stimulation signal generator comprises a digital to analog converter configured to convert the stimulation parameters into the stimulation signal, or convert the modified stimulation parameters into the modified stimulation signal.

20. The stimulator of claim 11, wherein
the stimulator comprises a neurostimulator or a muscular stimulator.

* * * * *